(12) United States Patent
McKinley

(10) Patent No.: US 7,799,081 B2
(45) Date of Patent: Sep. 21, 2010

(54) SYSTEM AND METHOD FOR SPINAL FUSION

(75) Inventor: Laurence M. McKinley, Escondido, CA (US)

(73) Assignee: Aeolin, LLC, Escondido, CA (US)

( * ) Notice: Subject to any disclaimer, the term of this patent is extended or adjusted under 35 U.S.C. 154(b) by 838 days.

(21) Appl. No.: 10/940,570

(22) Filed: Sep. 14, 2004

(65) Prior Publication Data

US 2006/0058876 A1    Mar. 16, 2006

(51) Int. Cl.
    *A61F 2/44* (2006.01)
(52) U.S. Cl. .................................. 623/17.16
(58) Field of Classification Search .............. 606/90, 606/105, 246; 623/17.11–17.16
    See application file for complete search history.

(56) References Cited

U.S. PATENT DOCUMENTS

| 4,501,269 | A |   | 2/1985  | Bagby             |
|-----------|---|---|---------|-------------------|
| 4,961,740 | A |   | 10/1990 | Ray et al.        |
| 5,026,373 | A |   | 6/1991  | Ray et al.        |
| 5,055,104 | A |   | 10/1991 | Ray               |
| 5,108,438 | A |   | 4/1992  | Stone             |
| 5,258,043 | A |   | 11/1993 | Stone             |
| 5,389,291 | A |   | 2/1995  | Reiffenrath et al.|
| 5,415,661 | A |   | 5/1995  | Holmes            |
| 5,462,518 | A |   | 10/1995 | Hatley et al.     |
| 5,489,307 | A |   | 2/1996  | Kuslich et al.    |
| 5,514,180 | A |   | 5/1996  | Heggeness et al.  |
| 5,562,735 | A |   | 10/1996 | Margulies         |
| 5,609,635 | A | * | 3/1997  | Michelson ......... 623/17.16 |
| 5,645,084 | A |   | 7/1997  | McKay             |
| 5,645,598 | A |   | 7/1997  | Brosnahan, III    |
| 5,653,763 | A |   | 8/1997  | Errico et al.     |
| 5,665,122 | A |   | 9/1997  | Kambin            |
| 5,669,909 | A |   | 9/1997  | Zdeblick et al.   |
| 5,700,291 | A |   | 12/1997 | Kuslich et al.    |
| 5,700,292 | A |   | 12/1997 | Margulies         |
| 5,702,449 | A |   | 12/1997 | McKay             |

(Continued)

FOREIGN PATENT DOCUMENTS

FR    2726759    5/1996

(Continued)

OTHER PUBLICATIONS

European Search Report dated Dec. 15, 2005 for Application No. 05077059.3 (8 pgs).

*Primary Examiner*—Eduardo C Robert
*Assistant Examiner*—David Comstock
(74) *Attorney, Agent, or Firm*—Kauth, Pomeroy, Peck & Bailey LLP

(57) ABSTRACT

The current invention is directed to a system and method for fusing two adjacent vertebrae. In one embodiment, the vertebrae are fused by inserting a self-broaching interbody apparatus into a disc space without the need for separately drilling and broaching. The self-broaching interbody apparatus may include cutting flutes or other broaching means capable of cutting through the cartilaginous endplates of the vertebrae. In another embodiment, an interbody apparatus with an expanding means capable of distracting the disc space between the adjacent vertebrae is inserted into the disc space. Another embodiment includes a sleeve that fits around an interbody apparatus that has at least one opening in its outer surface leading to a cavity filled with bone and/or ortho-biological materials.

5 Claims, 6 Drawing Sheets

U.S. PATENT DOCUMENTS

| | | |
|---|---|---|
| 5,702,453 A | 12/1997 | Rabbe et al. |
| 5,702,455 A | 12/1997 | Saggar |
| 5,709,683 A | 1/1998 | Bagby |
| 5,749,916 A | 5/1998 | Richelsoph |
| 5,766,252 A | 6/1998 | Henry et al. |
| 5,776,197 A | 7/1998 | Rabbe et al. |
| 5,776,198 A | 7/1998 | Rabbe et al. |
| 5,776,253 A | 7/1998 | Asakawa et al. |
| 5,782,830 A | 7/1998 | Farris |
| 5,782,832 A | 7/1998 | Larsen et al. |
| 5,782,919 A | 7/1998 | Zdeblick et al. |
| 5,800,550 A | 9/1998 | Sertich |
| 5,865,847 A | 2/1999 | Kohrs et al. |
| 5,876,457 A | 3/1999 | Picha et al. |
| 5,885,299 A | 3/1999 | Winslow et al. |
| 5,904,719 A | 5/1999 | Errico et al. |
| 5,906,616 A | 5/1999 | Pavlov et al. |
| 5,910,315 A | 6/1999 | Stevenson et al. |
| 5,916,267 A | 6/1999 | Tienboon |
| 5,928,284 A | 7/1999 | Mehdizadeh |
| 5,941,880 A | 8/1999 | Errico et al. |
| 5,947,971 A | 9/1999 | Kuslich et al. |
| 5,968,098 A | 10/1999 | Winslow |
| 5,972,368 A | 10/1999 | McKay |
| 5,976,187 A | 11/1999 | Richelsoph |
| 5,984,967 A | 11/1999 | Zdeblick et al. |
| 5,989,250 A | 11/1999 | Wagner et al. |
| 6,004,326 A | 12/1999 | Castro et al. |
| 6,010,502 A | 1/2000 | Bagby |
| 6,033,405 A | 3/2000 | Winslow et al. |
| 6,033,438 A | 3/2000 | Bianchi et al. |
| 6,037,519 A | 3/2000 | McKay |
| 6,045,579 A | 4/2000 | Hochshuler et al. |
| 6,045,580 A | 4/2000 | Scarborough et al. |
| 6,059,790 A | 5/2000 | Sand et al. |
| 6,066,175 A | 5/2000 | Henderson et al. |
| 6,071,310 A | 6/2000 | Picha et al. |
| 6,080,193 A | 6/2000 | Hochshuler et al. |
| 6,086,595 A | 7/2000 | Yonemura et al. |
| 6,090,143 A | 7/2000 | Meriwether et al. |
| 6,096,080 A | 8/2000 | Nicholson et al. |
| 6,102,948 A | 8/2000 | Brosnahan, III |
| 6,102,950 A | 8/2000 | Vaccaro |
| 6,113,602 A | 9/2000 | Sand |
| 6,117,174 A | 9/2000 | Nolan |
| 6,126,688 A | 10/2000 | McDonnell |
| 6,126,689 A | 10/2000 | Brett |
| 6,127,597 A | 10/2000 | Beyar et al. |
| 6,129,763 A | 10/2000 | Chauvin et al. |
| 6,132,430 A | 10/2000 | Wagner |
| 6,136,031 A | 10/2000 | Middleton |
| 6,139,551 A | 10/2000 | Michelson et al. |
| 6,146,240 A | 11/2000 | Morris |
| 6,156,040 A | 12/2000 | Yonemura et al. |
| 6,159,244 A | 12/2000 | Suddaby |
| 6,159,245 A | 12/2000 | Meriwether et al. |
| 6,174,311 B1 | 1/2001 | Branch et al. |
| 6,174,334 B1 | 1/2001 | Suddaby |
| 6,183,517 B1 | 2/2001 | Suddaby |
| 6,190,414 B1 | 2/2001 | Young et al. |
| 6,193,755 B1 | 2/2001 | Metz-Stavenhagen et al. |
| 6,206,922 B1 | 3/2001 | Zdeblick et al. |
| 6,214,049 B1 | 4/2001 | Gayer et al. |
| 6,214,050 B1 | 4/2001 | Huene |
| 6,228,085 B1 | 5/2001 | Theken et al. |
| 6,231,609 B1 | 5/2001 | Mehdizadeh |
| 6,241,733 B1 | 6/2001 | Nicholson et al. |
| 6,241,769 B1 | 6/2001 | Nicholson et al. |
| 6,241,771 B1 | 6/2001 | Gresser et al. |
| 6,245,072 B1 | 6/2001 | Zdeblick et al. |
| 6,245,108 B1 | 6/2001 | Biscup |
| 6,248,106 B1 | 6/2001 | Ferree |
| 6,258,125 B1 | 7/2001 | Paul et al. |
| 6,261,293 B1 | 7/2001 | Nicholson et al. |
| 6,261,296 B1 | 7/2001 | Aebi et al. |
| 6,261,586 B1 | 7/2001 | McKay |
| 6,267,763 B1 | 7/2001 | Castro |
| 6,292,699 B1 | 9/2001 | Simon et al. |
| 6,296,664 B1 | 10/2001 | Middleton |
| 6,296,665 B1 | 10/2001 | Strnad et al. |
| 6,306,170 B2 | 10/2001 | Ray |
| 6,312,431 B1 | 11/2001 | Asfora |
| 6,315,795 B1 | 11/2001 | Scarborough et al. |
| 6,315,797 B1 | 11/2001 | Middleton |
| 6,325,827 B1 | 12/2001 | Lin |
| 6,332,894 B1 | 12/2001 | Stalcup et al. |
| 6,332,895 B1 | 12/2001 | Suddaby |
| 6,336,928 B1 | 1/2002 | Guerin et al. |
| 6,342,074 B1 | 1/2002 | Simpson |
| 6,344,057 B1 | 2/2002 | Rabbe et al. |
| 6,346,122 B1 | 2/2002 | Picha et al. |
| 6,346,123 B1 | 2/2002 | McKay |
| 6,371,986 B1 | 4/2002 | Bagby |
| 6,371,989 B1 | 4/2002 | Chauvin et al. |
| 6,375,655 B1 | 4/2002 | Zdeblick et al. |
| 6,383,221 B1 | 5/2002 | Scarborough et al. |
| 6,395,030 B1 | 5/2002 | Songer et al. |
| 6,395,035 B2 | 5/2002 | Bresina et al. |
| 6,409,765 B1 | 6/2002 | Bianchi et al. |
| 6,409,766 B1 | 6/2002 | Brett |
| 6,416,515 B1 | 7/2002 | Wagner |
| 6,423,095 B1 | 7/2002 | Van Hoeck et al. |
| 6,425,920 B1 | 7/2002 | Hamada |
| 6,428,541 B1 | 8/2002 | Boyd et al. |
| 6,428,575 B2 | 8/2002 | Koo et al. |
| 6,432,106 B1 | 8/2002 | Fraser |
| 6,432,107 B1 | 8/2002 | Ferree |
| 6,436,102 B1 | 8/2002 | Ralph et al. |
| 6,436,139 B1 | 8/2002 | Shapiro et al. |
| 6,436,140 B1 | 8/2002 | Liu et al. |
| 6,436,141 B2 | 8/2002 | Castro et al. |
| 6,436,142 B1 | 8/2002 | Paes et al. |
| 6,440,170 B1 | 8/2002 | Jackson |
| 6,443,987 B1 | 9/2002 | Bryan |
| 6,443,989 B1 | 9/2002 | Jackson |
| 6,443,990 B1 | 9/2002 | Aebi et al. |
| 6,447,512 B1 | 9/2002 | Landry et al. |
| 6,447,546 B1 | 9/2002 | Bramlet et al. |
| 6,451,019 B1 | 9/2002 | Zucherman et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,461,385 B1 | 10/2002 | Gayer et al. |
| 6,464,727 B1 | 10/2002 | Sharkey et al. |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,471,725 B1 | 10/2002 | Ralph et al. |
| 6,478,801 B1 | 11/2002 | Ralph et al. |
| 6,488,710 B2 | 12/2002 | Besselink |
| 6,491,695 B1 | 12/2002 | Roggenbuck |
| 6,491,724 B1 | 12/2002 | Ferree |
| 6,494,883 B1 | 12/2002 | Ferree |
| 6,500,206 B1 | 12/2002 | Bryan |
| 6,524,312 B2 | 2/2003 | Landry et al. |
| 6,527,805 B2 | 3/2003 | Studer et al. |
| 6,527,806 B2 | 3/2003 | Ralph et al. |
| 6,530,926 B1 | 3/2003 | Davison |
| 6,537,589 B1 | 3/2003 | Chae et al. |
| 6,547,823 B2 | 4/2003 | Scarborough et al. |
| 6,548,002 B2 | 4/2003 | Gresser et al. |
| 6,558,386 B1 | 5/2003 | Cragg |
| 6,558,387 B2 | 5/2003 | Errico et al. |

| | | |
|---|---|---|
| 6,558,424 B2 | 5/2003 | Thalgott |
| 6,562,040 B1 | 5/2003 | Wagner |
| 6,569,201 B2 | 5/2003 | Moumene et al. |
| 6,572,619 B2 | 6/2003 | Santilli |
| 6,575,981 B1 | 6/2003 | Boyd et al. |
| 6,576,016 B1 | 6/2003 | Hochshuler et al. |
| 6,579,321 B1 | 6/2003 | Gordon et al. |
| 6,582,431 B1 | 6/2003 | Ray |
| 6,582,433 B2 | 6/2003 | Yun |
| 6,582,437 B2 | 6/2003 | Dorchak et al. |
| 6,582,467 B1 | 6/2003 | Teitelbaum et al. |
| 6,595,992 B1 | 7/2003 | Wagner et al. |
| 6,595,995 B2 | 7/2003 | Zdeblick et al. |
| 6,599,292 B1 | 7/2003 | Ray |
| 6,599,320 B1 | 7/2003 | Kuslich et al. |
| 6,607,530 B1 | 8/2003 | Carl et al. |
| 6,610,065 B1 | 8/2003 | Branch et al. |
| 6,610,089 B1 | 8/2003 | Liu et al. |
| 6,610,092 B2 | 8/2003 | Ralph et al. |
| 6,613,050 B1 | 9/2003 | Wagner et al. |
| 6,613,091 B1 | 9/2003 | Zdeblick et al. |
| 6,616,671 B2 | 9/2003 | Landry et al. |
| 6,623,525 B2 | 9/2003 | Ralph et al. |
| 6,635,062 B2 | 10/2003 | Ray, III et al. |
| 6,635,086 B2 | 10/2003 | Lin |
| 6,638,310 B2 | 10/2003 | Lin et al. |
| 6,641,613 B2 | 11/2003 | Sennett |
| 6,641,614 B1 | 11/2003 | Wagner et al. |
| 6,645,206 B1 | 11/2003 | Zdeblick et al. |
| 6,645,211 B2 | 11/2003 | Magana |
| 6,645,249 B2 | 11/2003 | Ralph et al. |
| 6,648,895 B2 | 11/2003 | Burkus et al. |
| 6,648,915 B2 | 11/2003 | Sazy |
| 6,648,916 B1 | 11/2003 | McKay |
| 6,652,527 B2 | 11/2003 | Zucherman et al. |
| 6,652,593 B2 | 11/2003 | Boyer, II et al. |
| 6,656,178 B1 | 12/2003 | Veldhuizen et al. |
| 6,656,224 B2 | 12/2003 | Middleton |
| 6,666,888 B1 | 12/2003 | Jackson |
| 6,666,889 B1 | 12/2003 | Commarmond |
| 6,669,730 B2 | 12/2003 | Ralph et al. |
| 6,669,731 B2 | 12/2003 | Ralph et al. |
| 6,673,075 B2 | 1/2004 | Santilli |
| 6,673,113 B2 | 1/2004 | Ralph et al. |
| 6,676,703 B2 | 1/2004 | Biscup |
| 6,679,887 B2 | 1/2004 | Nicholson et al. |
| 6,682,561 B2 | 1/2004 | Songer et al. |
| 6,682,563 B2 | 1/2004 | Scharf |
| 6,685,742 B1 | 2/2004 | Jackson |
| 6,689,132 B2 | 2/2004 | Biscup |
| 6,689,167 B2 | 2/2004 | Bagby |
| 6,689,168 B2 | 2/2004 | Lieberman |
| 6,695,851 B2 | 2/2004 | Zdeblick et al. |
| 6,695,882 B2 | 2/2004 | Bianchi et al. |
| 6,696,073 B2 | 2/2004 | Boyce et al. |
| 6,699,288 B2 | 3/2004 | Moret |
| 6,706,070 B1 | 3/2004 | Wagner et al. |
| 6,712,825 B2 | 3/2004 | Aebi et al. |
| 6,719,760 B2 | 4/2004 | Dorchak et al. |
| 6,719,794 B2 | 4/2004 | Gerber et al. |
| 6,719,795 B1 | 4/2004 | Cornwall et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,723,127 B2 | 4/2004 | Ralph et al. |
| 6,726,720 B2 | 4/2004 | Ross et al. |
| 6,726,722 B2 | 4/2004 | Walkenhorst et al. |
| 6,736,849 B2 | 5/2004 | Li et al. |
| 6,740,117 B2 | 5/2004 | Ralph et al. |
| 6,743,234 B2 | 6/2004 | Burkus et al. |
| 6,743,255 B2 | 6/2004 | Ferree |
| 6,746,484 B1 | 6/2004 | Liu et al. |
| 6,758,861 B2 | 7/2004 | Ralph et al. |
| 6,758,862 B2 | 7/2004 | Berry et al. |
| 6,761,738 B1 | 7/2004 | Boyd |
| 6,764,515 B2 | 7/2004 | Ralph et al. |
| 6,767,366 B2 | 7/2004 | Lee et al. |
| 6,770,096 B2 | 8/2004 | Bolger et al. |
| 6,773,460 B2 | 8/2004 | Jackson |
| 6,776,800 B2 | 8/2004 | Boyer, II et al. |
| 6,783,545 B2 | 8/2004 | Castro et al. |
| 6,783,547 B2 | 8/2004 | Castro |
| 6,790,233 B2 | 9/2004 | Brodke et al. |
| RE38,614 E | 10/2004 | Paul et al. |
| 6,800,092 B1 | 10/2004 | Williams et al. |
| 6,800,093 B2 | 10/2004 | Nicholson et al. |
| 6,805,697 B1 | 10/2004 | Helm et al. |
| 6,805,716 B2 | 10/2004 | Ralph et al. |
| 6,814,738 B2 | 11/2004 | Naughton et al. |
| 6,821,298 B1 | 11/2004 | Jackson |
| 6,824,565 B2 | 11/2004 | Muhanna et al. |
| 6,830,570 B1 | 12/2004 | Frey et al. |
| 6,835,206 B2 | 12/2004 | Jackson |
| 6,835,208 B2 | 12/2004 | Marchosky |
| 6,837,904 B2 | 1/2005 | Ralph et al. |
| 6,840,941 B2 | 1/2005 | Rogers et al. |
| 6,843,804 B2 | 1/2005 | Bryan |
| 6,855,151 B2 | 2/2005 | Ralph et al. |
| 6,855,169 B2 | 2/2005 | Boyer, II et al. |
| 6,863,688 B2 | 3/2005 | Ralph et al. |
| 6,863,689 B2 | 3/2005 | Ralph et al. |
| 6,863,889 B2 | 3/2005 | Shimkets et al. |
| 6,869,446 B2 | 3/2005 | Ralph et al. |
| 6,887,273 B2 | 5/2005 | Ralph et al. |
| 6,887,274 B2 | 5/2005 | Ralph et al. |
| 6,893,462 B2 | 5/2005 | Buskirk et al. |
| 6,893,464 B2 | 5/2005 | Kiester |
| 6,893,465 B2 | 5/2005 | Huang |
| 6,899,714 B2 | 5/2005 | Vaughan |
| 6,899,716 B2 | 5/2005 | Cragg |
| 6,902,580 B2 | 6/2005 | Fallin et al. |
| 6,902,581 B2 | 6/2005 | Walkenhorst et al. |
| 6,905,512 B2 | 6/2005 | Paes et al. |
| 6,918,934 B2 | 7/2005 | Ralph et al. |
| 6,921,403 B2 | 7/2005 | Cragg et al. |
| 6,923,811 B1 | 8/2005 | Carl et al. |
| 6,926,737 B2 | 8/2005 | Jackson |
| 6,929,647 B2 | 8/2005 | Cohen |
| 6,932,884 B2 | 8/2005 | Saito et al. |
| 6,936,070 B1 | 8/2005 | Muhanna |
| 7,211,112 B2 * | 5/2007 | Baynham et al. .......... 623/17.11 |
| 7,217,291 B2 * | 5/2007 | Zucherman et al. ...... 623/17.15 |
| 2003/0065396 A1 * | 4/2003 | Michelson ............... 623/17.15 |

FOREIGN PATENT DOCUMENTS

| | | |
|---|---|---|
| FR | 2803741 | 7/2001 |
| WO | WO98/17209 | 4/1998 |
| WO | WO00/25707 | 5/2000 |
| WO | WO01/91686 | 12/2001 |
| WO | WO03/032812 A2 | 4/2003 |

* cited by examiner

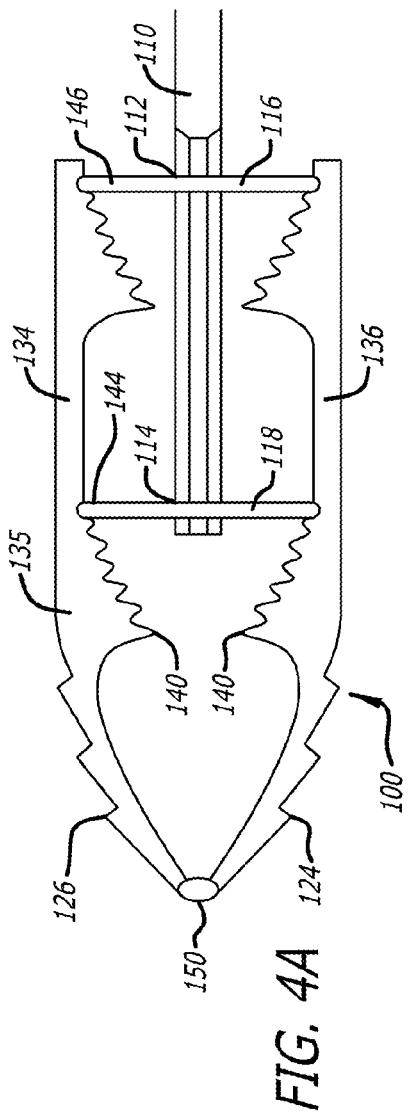
FIG. 4A
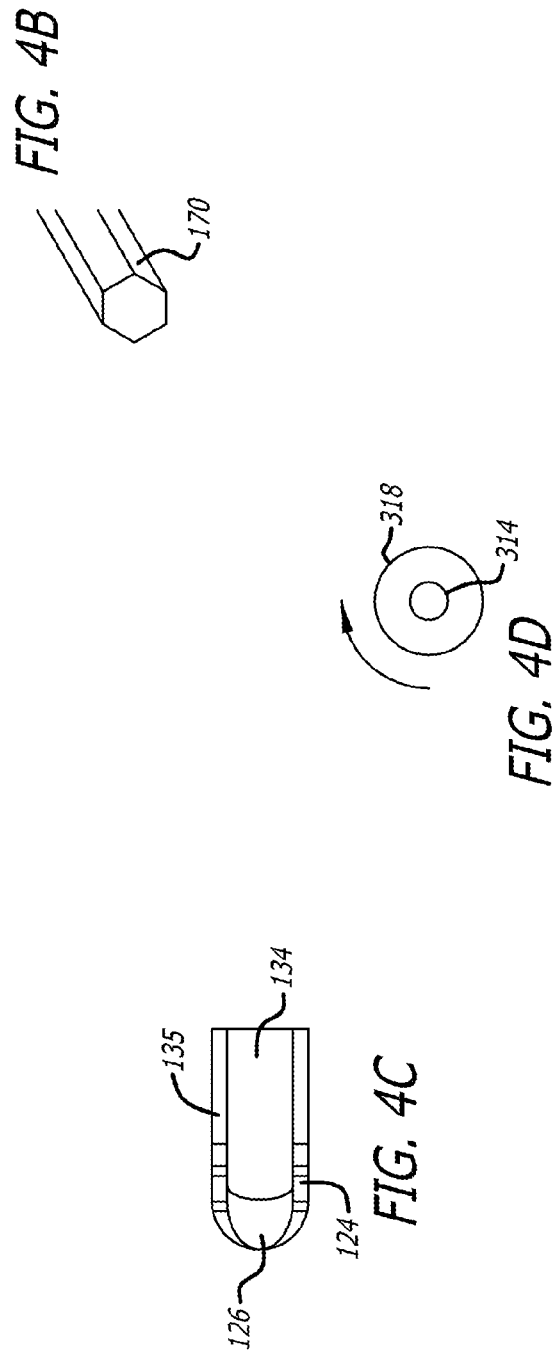
FIG. 4B
FIG. 4D
FIG. 4C

SYSTEM AND METHOD FOR SPINAL FUSION

BACKGROUND

As the lumbar spine ages, disc degeneration occurs. This degeneration causes a reduction in the vertical height of the disc, and a diminution of its viscoelastic properties. The profile of the spine also changes with age. The swayback curvature of youth becomes the flat-back of old age. This results in increased biomechanical stress on the posterior side of the spine.

With a recent increased understanding in the biomechanics of the spine, it is acknowledged that maintenance of the normal curvature of the lumbar spine is preferable. When spinal fusions are considered, it is important to re-establish the normal biomechanical arrangement, and to restore the sagittal profile of the spine to obtain optimal results. Arthritic changes in the facet joints following disc degeneration can cause mechanical back pain. If they become excessive, these arthritic changes can cause spinal stenosis.

For these reasons, several prior art techniques have been used that remove the degenerated disc, distract the disc space, and rigidly bond the upper and lower adjacent vertebrae together. Initially, this was accomplished by inserting pieces of bone having cortex and marrow cut from solid bone locations, such as the wing of the pelvis or the fibula. Such grafts were only able to support around 430 lbs. of force within the disc space, however, and compression forces up to 1,850 lbs. can be experienced by a human when, for example, bending over to pick up a 25 lb. child. After experiencing such high compression forces, these grafts tended to collapse and lose their ability to fix and stabilize the spinal motion segment by distracting the disc space.

To deal with this problem, metal cages packed with bone or ortho-biological compounds (osteoinductive/osteoconductive) capable of fusing with the adjacent vertebrae were inserted in the distracted disc space. Such cages were able to withstand the larger compression forces while allowing the bone inside of the cages to fuse with the adjacent vertebrae. The cages were typically constructed of titanium mesh cylinders, screw-in bullet-like metal cages with external threads, or rectangular cages made of carbon fiber.

These cages were typically inserted into the disc space after the space had been distracted and/or drilled by a separate tool to form a niche for the cage and to broach through the cartilage and into the boney tissue to promote fusion. For purposes of this disclosure "broaching" refers to cutting through the cartilage of adjacent vertebral endplates and into the boney tissue of the vertebrae. The process of separately broaching and distracting the disc space, however, requires multiple steps of inserting and removing various drills, broaches and/or distracters into the disc space, causing direct or indirect damage to the load-bearing endplates of the adjacent vertebrae, weakening them and jeopardizing the fixation of the interbody fusion construction.

Because of the openings in the cages, another problem with the prior art cages were that small pieces of bone or ortho-biological material were capable of spilling out of the cage and into the soft tissue surrounding the surgical opening before the cage was placed between the vertebral endplates. In this case, heterotrophic ossification, or bone growth, could occur in the access port of the surgical wound or possibly near the exiting segmental nerve, resulting in bony nerve entrapment and tremendous pain and complications.

Other prior art methods of distracting the disc space included inserting a semi-rigid, U-shaped object with internal teeth. A round object with a larger diameter than the interior space of the object was then inserted into the interior space between facing interior teeth. By moving the round object further into the interior of the object, the legs of the U-shaped object were pushed apart, thereby distracting the disc space. These U-shaped devices, however, typically broke due to the forces exerted by the round object and the adjacent vertebrae.

In addition to the above problems with inserting the prior art cages, the cages are susceptible to movement within the disc space once they are inserted. This movement can damage the biological growth of the fusion, due to shear forces on the vascular ingrowth nourishing the endosteal bone growth—limiting the development of fusion of the bone inside of the cage which is necessary to stabilize the adjacent vertebrae, resulting in looseness and bone graft collapse. To this effect, several prior art cages were constructed with short spikes or points to stabilize them within the disc space, but which were not long enough to broach through the cartilage into the boney tissue of the vertebrae.

Moreover, if the compression forces are not withstood and the disc space is not held in a distracted state by a strong cage, the cage may collapse, leading to looseness, instability and further failure of fusion due to movement. However, if the cage is overly rigid and strong, such as a threaded cage, it may shield the bone inside of the cage from the normal stresses and strains that bone needs to develop into weight bearing, trabecular bone, which will fuse with the adjacent vertebrae in a strong and rigid fashion. This failure to satisfactorily promote fusion may also lead to looseness and instability of the cage or fusion construct.

Therefore, a need exists to provide an interbody device or a method of inserting such a device that solves one or more of the problems described above.

SUMMARY OF THE INVENTION

The current invention is directed to a system and method for fusing a first and second vertebra. In one embodiment, the vertebrae are fused by inserting a self-broaching interbody device into a disc space without the need for separately drilling and broaching. The self-broaching interbody device may include cutting flutes or other broaching means capable of cutting through the cartilaginous endplates of the vertebrae–exposing subchondial bone, facilitating fusion development.

In another embodiment, an interbody device with an expanding means is inserted into the disc space. The expanding means is capable of moving the interbody device from an unexpanded state, where the upper and lower surfaces of the interbody device are at a first distance from each other, to an expanded state, where the upper and lower surfaces are at a second and greater distance from each other. In the unexpanded state, the interbody device can be inserted between the vertebrae while they are in an undistracted state without the need for previously distracting the disc space. In the expanded state, the inserted interbody device can force the first and second vertebrae into a distracted state.

Yet another embodiment includes a sleeve that fits around an interbody device that has at least one opening in its outer surface leading to a cavity. Bone graft and/or ortho-biological materials capable of fusing with the vertebrae are contained within the sleeve's cavity. The sleeve is configured to fit around the interbody device so that the biological materials are kept within the cavity while the interbody device is within the sleeve. The interbody device can then by moved completely through the sleeve to rest between the vertebrae.

BRIEF DESCRIPTION OF THE DRAWINGS

These and other features and advantages of the present invention will be better understood by reference to the following detailed description when considered in conjunction with the accompanying drawings where:

FIG. 4a is a side cross-sectional view of another embodiment of an interbody system according to the invention;

FIG. 4b is a front perspective view of an end of the insertion rod shown in FIG. 4a;

FIG. 4c is a top view of the embodiment shown in FIG. 4a;

FIG. 4d is an alternate embodiment of the middle septum shown in FIG. 4a;

DETAILED DESCRIPTION OF THE EXEMPLARY EMBODIMENTS

Figure 1:
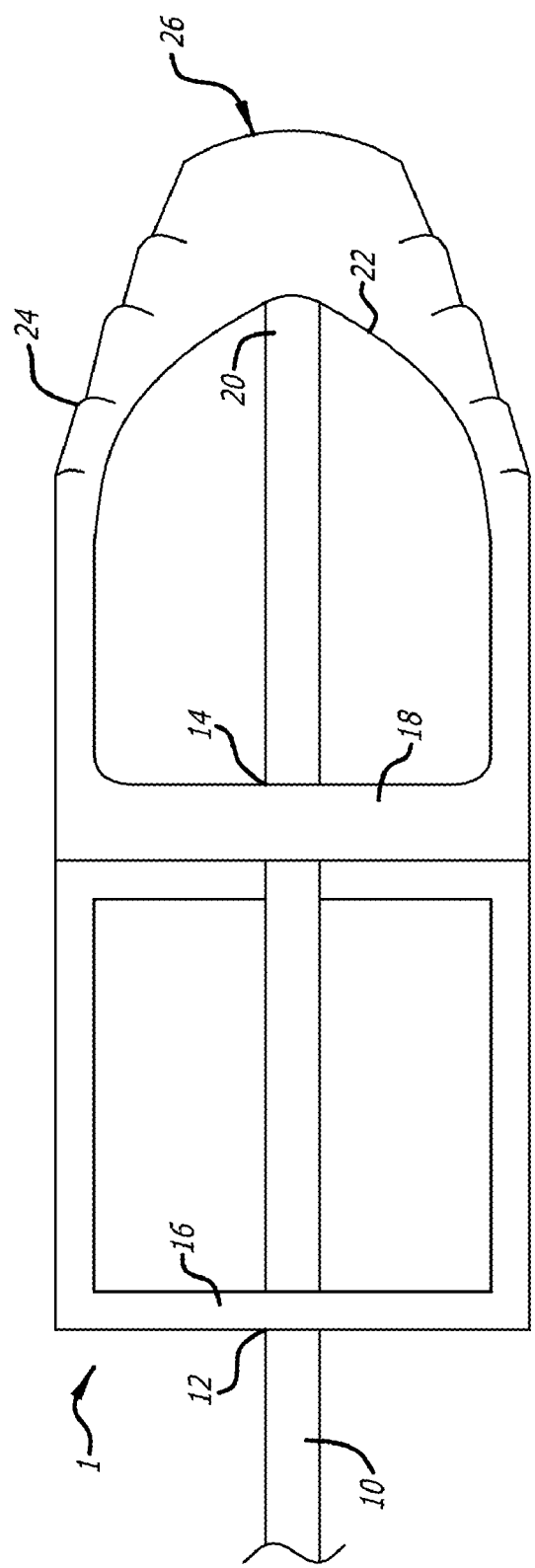
FIG. 1 is a top view of one embodiment of an interbody system according to the invention.

FIG. 1 shows a top view of an interbody cage 1 and an insertion rod 10. The cage 1 includes a substantially square and hollow main portion 2 and a nose 26. Bone graft with biological materials, such as morphogenic protein and derivatives, can be placed inside of the cage 1 to allow the cage 1 to be fused and incorporated into the boney structure of the adjacent vertebrae once the cage 1 is inserted.

The insertion rod 10 projects through axial openings 12 and 14 of the back wall 16 and middle septum 18, respectively, of the cage 1. A distal end 20 of the insertion rod 10 abuts an internal, distal end 22 of the cage 1, and is shaped to match the internal, distal end 22 of the cage 1. This shape serves to evenly distribute an insertion force exerted by the insertion rod 10 onto the internal, distal end 22 of the cage 1.

The middle septum 18 of the cage L comprises a rigid girder fixed to the interior surface of the cage 1 and located in a plane transverse to the projection of the insertion rod 10. The middle septum 18 serves to stabilize the insertion rod 10 and to increase the center strength of the generally hollow cage 1. The middle septum 18 may also include internal threads that mate with external threads on the insertion rod 10. Mating of these threads can more evenly distribute the force exerted on the insertion rod to the cage 1. In other embodiments of the cage, the middle septum 18 is not included or is replaced by several girders disposed on either side of the insertion rod.

The back wall 16 can be double welded to the back edge of the cage 1 to allow for increased vertical and horizontal strength of the cage 1. The opening 12 in the back wall 16 may alternatively include internal threads that can mate with external threads on the inserting rod 10. In this embodiment, the mating of the threads can aid in the insertion force transmitted from the inserting rod 10 to the cage 1.

In this embodiment, the cage 1 has a generally parabolic nose 26. The parabolic shape can aid in the distraction of the disc space between the adjacent vertebrae (shown in FIG. 2) by slowly separating them vertically as the nose 26 is inserted into the disc space.

Figure 2:
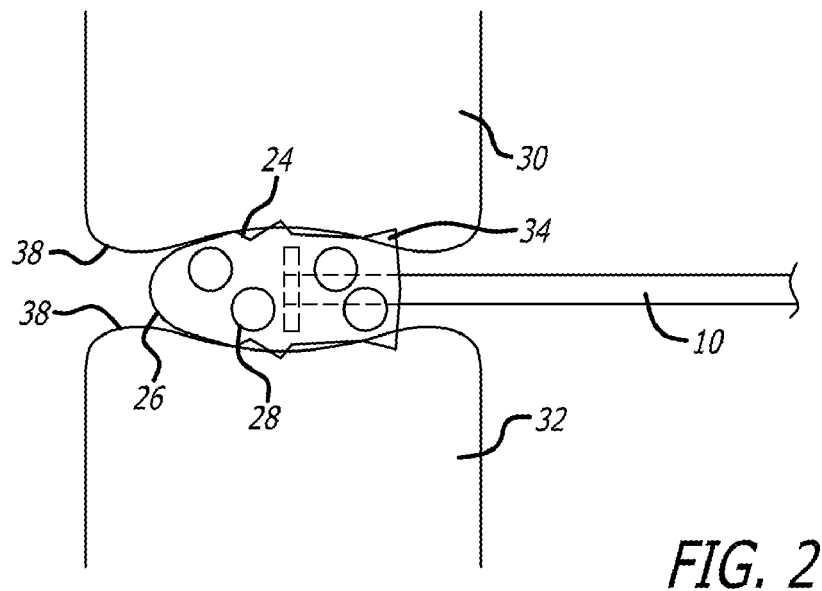
FIG. 2 is a side view of the embodiment shown in FIG. 1, inserted into adjacent vertebrae.

As shown in the side view of FIG. 2, the cage 1 has fenestrations 28, or openings, along its sides. These fenestrations allow bone graft within the main portion 2 to fuse with adjacent vertebrae outside of the cage 1.

Cutting flutes 24 are disposed in two lines along each upper and lower sides of the nose 26. The cutting flutes 24 project from the nose 26 in a generally vertical direction, in a manner similar to a Sampson nail. The cutting flutes 24 are long enough to broach through the cartilage of the vertebral endplates and into the boney tissue. For purposes of this disclosure, "self-broaching" refers to the interbody device's ability to broach through the cartilaginous endplates of a vertebra on its own, exposing subchondral bone. In one embodiment, the flutes 24 are between 1-3 mm long. By broaching into the vertebrae, the cage 1 can allow the blood and tissue from the adjacent vertebrae to mix with the bone graft within the cage 1 to promote fusion.

As the cage 1 is inserted postero-laterally in the disc space between upper and lower adjacent vertebrae 30 and 32, the nose 26 slowly distracts the disc space between the vertebrae 30 and 32 as the insertion rod 10 is pushed in the insertion direction. The distracting cage 1 also protects the load-bearing endplates 38 of the adjacent vertebrae 30 and 32 from damage resulting from prior art distraction and drilling methods.

As the cage 1 slides along the adjacent vertebrae, the cutting flutes 24 cut tracks 34 into the adjacent vertebrae 30 and 32. In this embodiment, keel edges 35 are disposed along in two lines along each of the upper and lower sides of the main portion 2, which trail behind the cutting flutes 24 within the tracks 34 to maintain the alignment of the cage 1 with the adjacent vertebrae 30 and 32. In addition to cutting tracks 34 for alignment purposes, cutting flutes 24 broach into the vertebrae 30 and 32, releasing blood and tissue, which aid in the fusion of the bone graft located within the cage 1.

Figure 3:
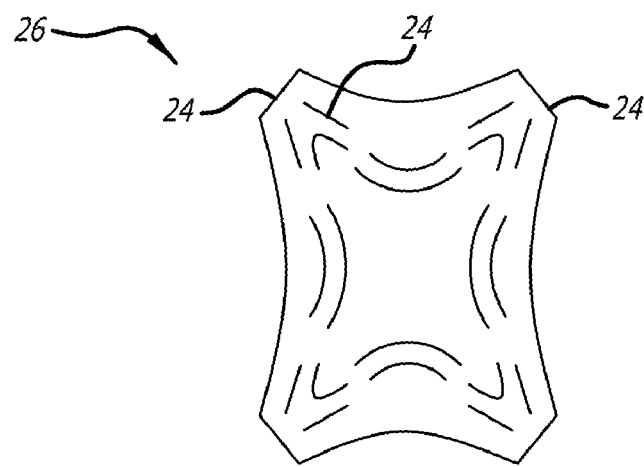
FIG. 3 is a front view of the nose of the embodiment shown in FIGS. 1 and 2.

A front view of the nose 26 is shown in FIG. 3. The top, bottom and side surfaces of the nose 26 are concave, with the cutting flutes 24 extending vertically outward from the center of the nose 26. This concavity allows the cutting flutes 24 to slide into the disc space with minimal friction, reducing the chances of hang up.

The substantially parabolic, fluted nose 26 allows the cage 1 to be self-broaching and self-aligning as it is pushed into the disc space by the insertion rod 10. This allows the preliminary steps of separately distracting the disc space and/or drilling an opening in the disc space to be eliminated. A second cage can then be inserted postero-laterally into the disc space, and additional bone graft inserted between the cages.

The nose can also include a central opening (not shown) to allow for anterior extraction or correction of the cage 1. In this embodiment, a threaded insertion rod 10 is inserted through this opening and threaded into threaded openings 14 and 12 in the middle septum 18 and back wall 16, respectively. The insertion rod 10 can then be pulled anteriorly to pull the cage 1 out from the disc space or to push the cage 1 into better alignment within the disc space.

In this embodiment, the cutting flutes 24 of the self-broaching cage 1 can cut tracks in the adjacent vertebrae to guide the cage 1 into place and expose bleeding subchondral bone to facilitate vascular ingrowth and promote fusion. In addition, the cutting flutes 24 can lock the cage 1 in place after the disc space is distracted.

Figure 8:
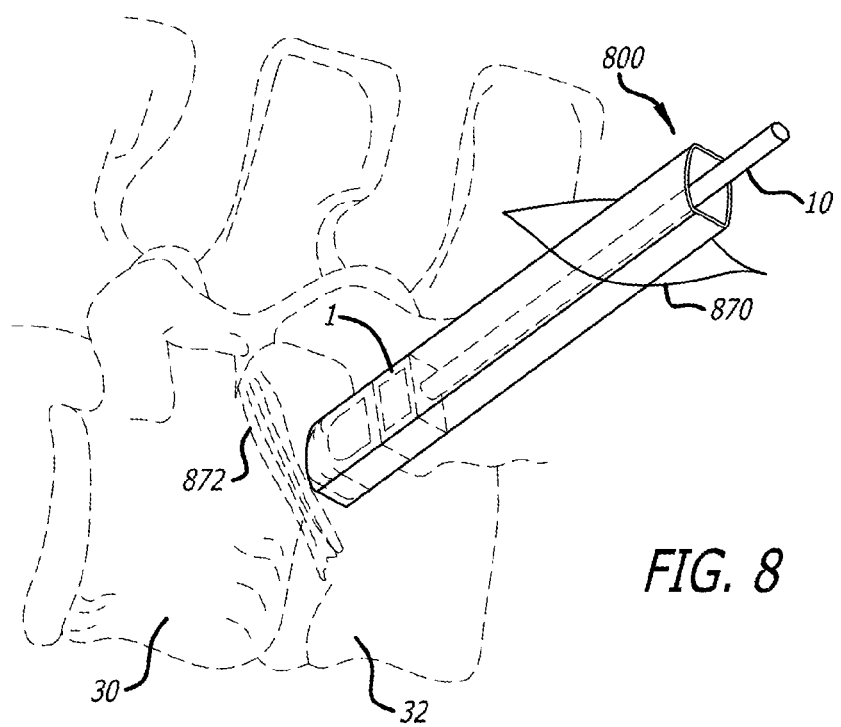
FIG. 8 is a side perspective view of an alternate embodiment of the invention inserted into a surgical opening toward the spine.

A sleeve 800, shown in FIG. 8, may be fitted around the cage 1 to cover the fenestrations 28 and open areas of the cage 1 and to keep the bone graft from exiting the cage 1 before the cage 1 is seated between the vertebrae 30 and 32. The sleeve 800 is substantially the same length as the insertion rod 110. The sleeve 800 surrounds the cage 1 and is inserted into a surgical opening 870, directed toward the vertebrae 30 and 32, avoiding the exiting nerve root 872. As the cage 1 is inserted into the disc space by passing through the sleeve 800, the sleeve 800 is slowly retracted or kept in place by abutting the adjacent vertebrae, allowing the bone graft to be released in the disc space.

Although the embodiment shown in FIG. 8 shows a sleeve 800 with a substantially rectangular cross-section, it is within the scope of the invention to form the sleeve with any shaped cross section. Preferably, the outer surface of the sleeve is shaped to provide easy insertion into the surgical opening or speculum (not shown), if one is present. The inner surface cross-sectional dimensions of the sleeve are preferably substantially the same as the outer surface dimensions of the cage, for example, extending approximately 0.5 mm to 3 mm to either side of the prosthesis, and more preferably about 1 mm to ether side.

The sleeve can be made of rigid plastic or any other suitable material, such as flexible plastic, metal, or bio-absorbable implant materials. In this embodiment, the sleeve 800 can not only prevent the bone graft from escaping from the cage 1 before insertion into the disc space, but can also protect the soft tissues and nerves surrounding the insertion path from damage. Preventing pieces of bone and ortho-biological material from falling into the approach wound can be important as bone can otherwise grow spontaneously if lost in the soft tissue, particularly if it grew around an exiting segmental nerve. Thus, the embodiment of the snugly-fitting sleeve 800 can contain and seal the prosthesis until it has docked in the disc space, substantially avoiding the possibility of heterotropic ossification.

In the embodiment shown in FIGS. 4a-4c, the cage 100 is also progressively self-distracting. Similar to the embodiment shown in FIGS. 1-3, the cage 100 includes cutting flutes 124 and fenestrated side walls with upwardly projecting keel edges 135. The cage 100 also includes upper and lower surfaces 134 and 136 that are vertically movable relative to each other. The upper and lower surfaces 134 and 136 include two sets of internal threads 140 and 142, each set having a space separating them that increases toward the nose 126. A middle septum 118 has external threads 144 that mate with the internal threads 140 of the upper and lower surfaces 134 and 136. A back wall 116 also has external threads 146 that mate with the internal threads 142 of the upper and lower surfaces 134 and 136.

Both the middle septum 118 and the back wall 116 have hexagonal central openings 114 and 112. An insertion rod 110 has a hexagonal cross section along its axis that, when inserted through the central openings 112 and 114 and rotated, rotates the middle septum 118 and the back wall 116 within the threads 142 and 144. As the middle septum 118 and back wall 116 are threaded closer to the nose 126, upper and lower surfaces 134 and 136 are pushed farther away from each other. As the surfaces 134 and 136 are pushed apart vertically, they distract the disc space further, correcting the alignment of the spine and locking the cage 100 in place between the adjacent vertebrae. This distraction is preferably gradual and progressive, produced by the application of measured and calibrated torque. This allows the surgeon to tailor the distraction to the individual patient and to predict with relative certainty the distraction produced by a given amount of torque. Progressive distraction additionally tightens the anatomy and ensures stability.

Anterior opening 150 in the nose 126 allows an insertion rod 110 to be inserted from the anterior side of the spine into the cage 100. If a surgeon desires to change the distraction of the disc space or to remove or change the position of the cage 100, the insertion rod 110 can again be inserted through openings 114 and 112, and rotated to thread the back wall 116 and middle septum 118 away from the nose 126, thus collapsing the space between surfaces 134 and 136.

In FIG. 4d, an oblong cam 318 is shown that can be used in place of the threaded middle septum 118 and internal threads 140. Oblong cam 318 can be rotated within an internal groove (not shown) in a cage to have its longer diameter aligned vertically. Small slits can be made in the upper and lower surfaces through which the tips of the oblong cam 318 would extend when it is vertically aligned. Because of the force from the adjacent vertebrae when the cage is in an expanded state, the slits in the upper and lower surfaces would lock the oblong cam in vertical alignment once the tips of the oblong cam 318 pass the slits. A similar oblong cam can be used to replace the back wall 116 and internal threads 142 in the embodiment shown in FIG. 4a.

Figure 5:
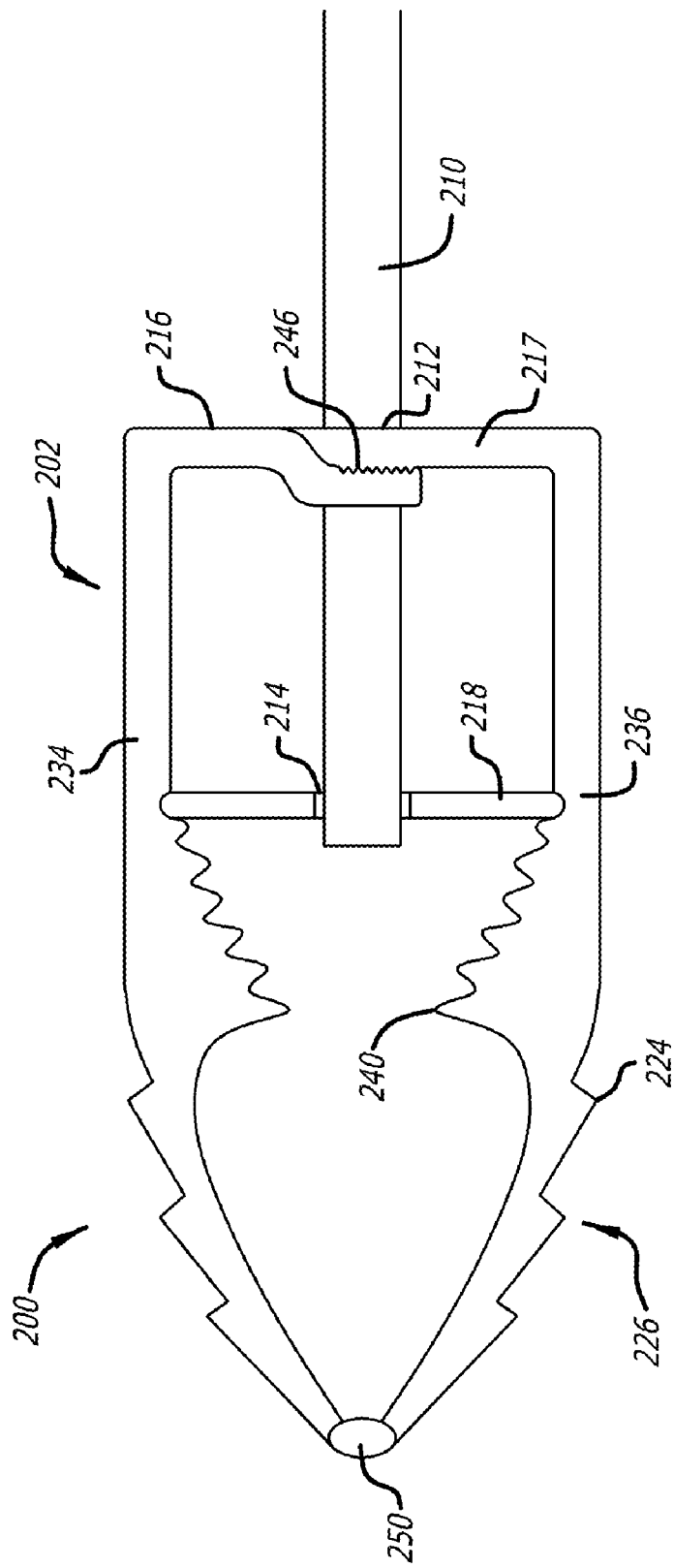
FIG. 5 is a side cross-sectional view of another embodiment of an interbody cage system according to the invention.

FIG. 5 shows another embodiment of a self-broaching and self-distracting cage 200. Cutting flutes 224 are aligned along nose 226 in a manner similar to the embodiment shown in FIGS. 1-3 to allow the cage 200 to be self-broaching. Cage 200 also includes a threaded middle septum 218 within internal threads 240 that converge toward the nose 226, similar to the middle septum 118 shown in FIG. 4a.

In this embodiment, the back walls 216 and 217 are formed as overlapping rectangles that each have a groove-type opening 212, allowing the insertion rod 210 to project through the overlapping area. The overlapping portions of back walls 216 and 217 have interlocking teeth 246. The interlocking teeth 246 of each of the back walls 216 and 217 project toward the other of the back walls 217 and 216 so that, when the upper and lower surfaces 234 and 236 move away from each other, they ratchet up the vertical height of the posterior side of the cage 200 until the corners of the back walls 217 and 216 indent into the adjacent vertebrae to stop the cage from extruding from the disc space.

By locking the vertical height of the posterior side of the cage 200, the force on the cage 200 from the distraction of the disc space is distributed along the main portion 202 of the cage 200, making collapse of the cage 200 due to those forces less likely.

If a surgeon wishes to remove the cage 200, the insertion rod 210 can be inserted through anterior opening 250, and openings 214 and 212 to rotate the middle septum 218 so that it is threaded away from the nose 226, collapsing the center portion of the cage 200. The insertion rod or a screwdriver-type tool can be used that would allow a surgeon to disconnect the interlocking teeth 246 by tapping or flicking the back walls to disengage the teeth. When the teeth are disengaged, the force on the back walls would then bend them into a V-shape after the center portion of the cage 200 is collapsed.

In each of the embodiments discussed above, the fenestrated walls of the cage can be cut or stamped out from metal or absorbable biological material mesh prior to cage formation. Preferably, the metal would be titanium, stainless steel, alloys or carbon fiber. Alloys such as porous titanium-nickel alloy have been shown to promote rapid tissue ingrowth.

The cutting flutes or keel pieces can be formed by cutting the fenestrated metal in a line that passes through several of the fenestrations. This results in an edge with several sharp protrusions. This edge can then be electrostatically welded to another similar edge for increased strength.

Although one skilled in the art will understand that the dimensions of the cages and insertion rods can be varied for the desired result, it has been found that a length of between 22 mm and 30 mm, a height of between 8 mm and 19 mm, and a transverse diameter of 8 mm to 12 mm is ideal. The cages are preferably of graduated sizes to accommodate the variation of human anatomical size. The vertical height in the distracting embodiments may increase an additional 1.5 mm in each direction.

Figure 6:
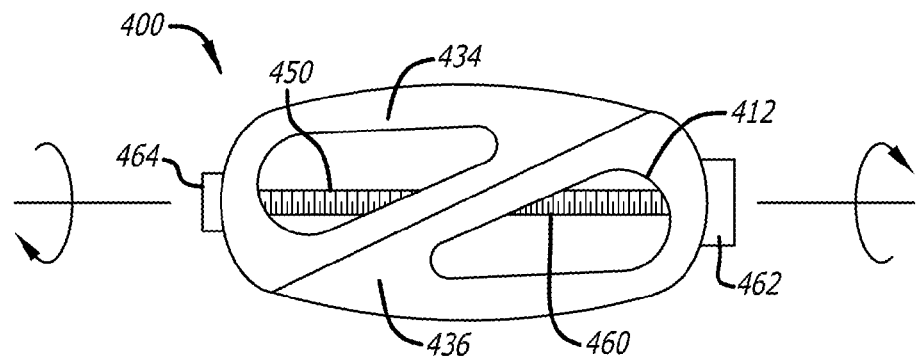
FIG. 6 is a side perspective view of yet another embodiment of an interbody cage system according to the invention.

FIG. 6 shows another embodiment of a self-distracting cage 400. In this embodiment, the cage 400 is formed from two wedge-shaped, hollow portions 434 and 436. A screw 460 projects through internal threads in the anterior and posterior openings 450 and 412 and has a screw head 462 and 464 at both ends so that the screw 460 cannot disengage with the threads of either opening 450 or 412.

The screw heads 462 and 464 can mate a screw driver (not shown) to be rotated while inside of the disc space. As the screw 460 is rotated within the threads of openings 450 and 412, the wedge-shaped portions 434 and 436 slide over each other and distract the disc space. The screw heads 462 and 464 can be rotated either posteriorly or anteriorly to distract or collapse the disc space.

Figure 7A:
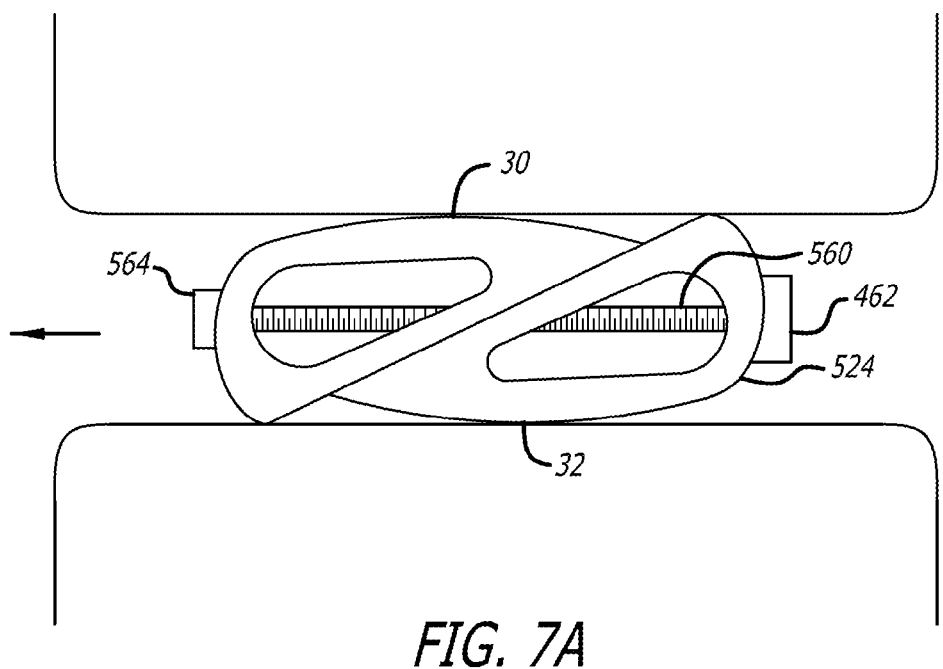
FIG. 7a is a side perspective view of still yet another embodiment of an interbody cage system according to the invention in an unexpanded state.
Figure 7B:
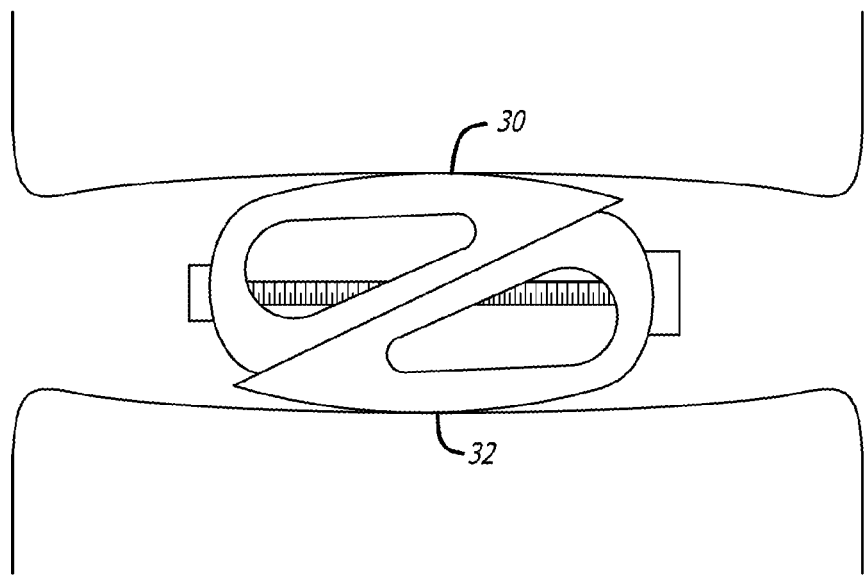
FIG. 7b is a side perspective view of the embodiment shown in FIG. 7a in an expanded state.

FIGS. 7a and 7b show an alternate embodiment of the slip-wedge cage shown in FIG. 6. In this embodiment, the cage 500 has domed and self-broaching wedge-shaped portions 534 and 536. Cutting flutes 524 project vertically in two lines along each of the top and bottom wedge-shaped portions 534 and 536, similar to the cutting flutes of the previous embodiments.

As the cage 500 is being inserted between adjacent vertebrae, the wedge-shaped portions 534 and 536 have only a minimal overlap, to ensure that the cage can be inserted into the disc space with its self-broaching cutting flutes 524 with minimal resistance. Once the cage is between the adjacent vertebrae 30 and 32, the screw 560 can be rotated by a screw driver (not shown) to pull the wedge-shaped portions toward each other, to distract the disc space. The dome shaped portions 534 and 536 allow the force of distraction to be evenly distributed across the cage, making unintentional collapse less likely.

In each of the embodiments discussed above, reflective fiducials can be added to the cage and the insertion rod to allow them to be used in image guided surgery.

Although specific embodiments are disclosed herein, it is expected that persons skilled in the art can and will design alternate embodiments and methods that are within the scope of the following claims either literally or under the doctrine of equivalents.

What is claimed is:

1. A spinal fusion system for fusing two adjacent vertebrae, comprising:

a self-broaching interbody apparatus with an upper surface, a llower surface, an insertion end and a trailing end; and an expanding means comprising;

a first end wall projecting from the upper surface on one of the insertion end and the trailing end toward the lower surface and having a first opening with internal threads;

a second end wall projecting from the lower surface on the other of the insertion end and the trailing end toward the upper surface and having a second opening with internal threads;

first and second sidewalls having first and second projecting edges, the first and second sidewalls fixed to the upper surface and the first end wall, and increasing in size toward the first end wall;

third and fourth sidewalls having third and fourth projecting edges, the third and forth sidewalls fixed to the lower surface and the second end wall, and increasing in size toward the second end wall; and a linking screw with external threads that mate with the internal threads of the first and second end walls, such that when the linking screw is rotated the first and second end walls are pulled toward each other causing the first and third projecting edges to slide against each other and the second and fourth projecting edges to slide against each other, wherein during such rotation the interbody apparatus is moved from an unexpanded state, where the upper and lower surfaces are at a first distance from each other, to an expanded state, where the upper and lower surfaces are at a second and greater distance from each other; and wherein in the unexpanded state, the interbody apparatus can be inserted between said adjacent vertebrae while the adjacent vertebrae are in an undistracted state, and in the expanded state, the interbody apparatus increases the distance between the adjacent vertebrae such that the vertebrae are in a distracted state.

2. The spinal fusion system of claim 1, wherein the insertion end includes cutting flutes, the cutting flutes projecting from the outside surface in a first direction and configured to cut through a cartilage layer on at least one of said adjacent vertebrae.

3. The spinal fusion system of claim 2, further comprising a keel projecting in substantially the first direction, fixed to the outside surface and aligned behind at least one of the cutting flutes.

4. The spinal fusion system of claim 1, wherein the trailing end includes an edge that projects at least partially outward, such that when the interbody apparatus sits between said adjacent vertebrae, the edge exerts force on said adjacent vertebrae.

5. The spinal fusion system of claim 1, wherein the upper and lower surfaces are curved to mate with said adjacent vertebrae.

* * * * *